United States Patent [19]

Pelavin

[11] 4,210,809

[45] Jul. 1, 1980

[54] METHOD AND APPARATUS FOR THE NON-INVASIVE DETERMINATION OF THE CHARACTERISTICS OF A SEGMENTED FLUID STREAM

[75] Inventor: Milton H. Pelavin, Chappaqua, N.Y.

[73] Assignee: Technicon Instruments Corporation, Tarrytown, N.Y.

[21] Appl. No.: 21,034

[22] Filed: Mar. 16, 1979

[51] Int. Cl.² ............................................. G01N 21/26
[52] U.S. Cl. .................................... 250/343; 250/356
[58] Field of Search ............... 250/258, 343, 344, 345, 250/356, 357, 373, 432 R, 435; 73/194 E, 194 F, 204; 356/246, 408, 39, 51, 436

[56] References Cited

U.S. PATENT DOCUMENTS

| 2,797,149 | 6/1957 | Skeggs .................................. 356/246 |
| 3,241,432 | 3/1966 | Skeggs et al. ....................... 356/408 |
| 3,842,670 | 10/1974 | Brain ..................................... 250/356 |
| 3,881,351 | 5/1975 | Prachar ................................ 250/356 |

Primary Examiner—Davis L. Willis
Attorney, Agent, or Firm—S. P. Tedesco

[57] ABSTRACT

New and improved method and apparatus for the non-invasive detection of the respective segments and segment interfaces, and the non-invasive determination of the respective segment volumes, of a continuous segmented fluid stream flowing in a transparent conduit are disclosed and comprise means to irradiate the conduit and the flowing fluid stream with radiation energy of spectral content predetermined in accordance with the radiation energy absorbance and refraction characteristics of the fluid segments and the fluid segment-conduit interface, means to detect the radiation energy which is transmitted through the segments and conduit and provide signals indicative thereof, and signal processing means operatively associated with the detecting means and operable to process said signals and perform the stated functions in accordance therewith.

26 Claims, 11 Drawing Figures

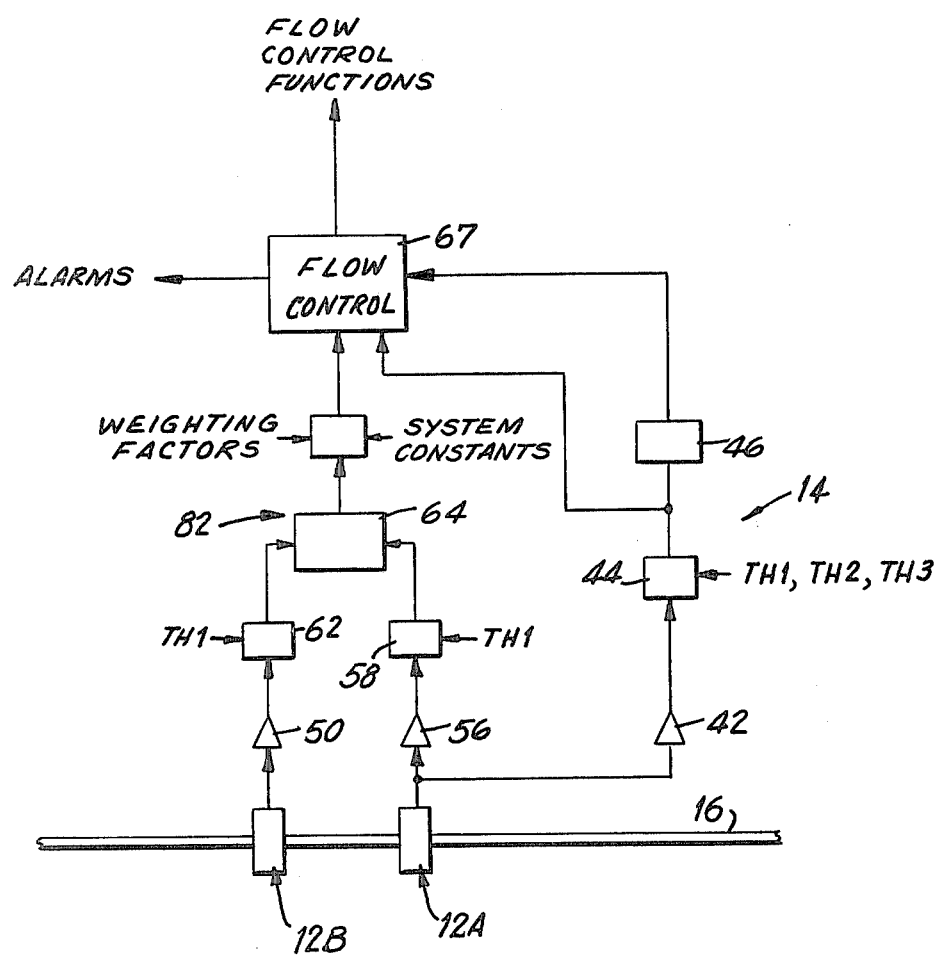

METHOD AND APPARATUS FOR THE NON-INVASIVE DETERMINATION OF THE CHARACTERISTICS OF A SEGMENTED FLUID STREAM

BACKGROUND OF THE INVENTION

1. Field of the Invention

This invention relates to new and improved method and apparatus for non-invasively detecting the gas-liquid interfaces and respective liquid and gas segments, in an air-segmented liquid stream flowing in a conduit, and for non-invasively determining the respective volumes of the liquid segments of said stream.

2. Description of the Prior Art

Although a number of methods and apparatus are known for detecting a variety of the flow and/or segment arrangement and number characteristics of air-segmented liquid streams flowing in conduits, the same usually require the location of detecting devices within the flow conduit, and are unsuitable for use in continuous flow automated analysis systems. More specifically, it will be appreciated that the presence of a detecting device in the flow conduit obstructs fluid flow in the conduit and degrades "wash" or causes contamination between successive segments. In addition, locating the detecting means in the flow conduit presents serious manufacturing problems, especially in those instances wherein internal diameter of the conduit is small; also, the calibration, relocation, and/or replacement of such detecting device can become particularly difficult. Too, and depending upon the chemical nature of the segmented stream liquid, chemical reaction between the liquid(s) under analysis and the detecting device can occur.

In addition, and although non-invasive methods and apparatus as above are known, they generally require the use of relatively sophisticated, expensive, and, in many instances, not particularly reliable components, which detract markedly from the overall value of those methods and apparatus, and especially in instances wherein the same are applied to automated biomedical analysis devices wherein particularly high standards of reliability must, of necessity, be met.

OBJECTS OF THE INVENTION

It is, accordingly, an object of this invention to provide new and improved, completely non-invasive method and apparatus for the detection of the gas-liquid interfaces, and the respective liquid and gas segments in a gas-segmented liquid stream flowing along a conduit.

Another object of this invention is to provide new and improved method and apparatus for the precise determination of liquid segment volumes in a gas-segmented liquid stream flowing at a substantially constant flow rate along a conduit.

Another object of this invention is the provision of new and improved method and apparatus for the determination, with a high degree of accuracy, of liquid segment volumes in a gas-segmented liquid stream flowing at varying flow rates along a conduit.

Another object of this invention is the provision of method and apparatus as above, which require the use of only relatively simple and inexpensive, readily available components of proven accuracy and dependability to insure relatively low apparatus cost and long periods of accurate and reliable operation.

Another object of this invention is the provision of apparatus, as above, which may be simply relocated relative to the flow conduit to take advantage of optimal fluid flow conditions in the flow conduit.

A further object of this invention is the provision of method and apparatus, as above, which are particularly, though by no means exclusively, adapted for use in automated, continuous flow blood analysis apparatus of the type described in U.S. Pat. Nos. 2,797,149 and 3,241,432, assigned to a common assignee.

An additional object of this invention is to provide method and apparatus for detecting gas-liquid interfaces, and the respective liquid and gas segments in a gas-segmented liquid stream flowing along a conduit, which is independent of the absorbance of such liquid.

DESCRIPTION OF THE DRAWINGS

The above and other objects and significant advantages of my invention are believed made clear by the following detailed description thereof taken in conjunction with the accompanying drawings wherein:

FIG. 9 is a schematic diagram illustrating concomitant segment interface detection and segment volume determination.

SUMMARY OF THE DISCLOSURE

As disclosed herein, the non-invasive method and apparatus for the detection of the gas-liquid interfaces, and of the respective volumes of the liquid and gas segments, of a gas segmented liquid stream are operatively disposed relative to an optically transparent conduit and comprise an IR (infra red) energy source and IR detector. Energy from the IR source passes through the conduit and to the IR detector. In operation differences in IR energy refraction and/or absorption characteristics of the gas, liquid and marker liquid segments are detected and processed to determine the number and disposition of such segments in the stream. Precise determination of the liquid segment volume is achieved by disposing two of the apparatuses of the invention at precisely spaced locations along the flow conduit.

The precise liquid segment volume determination is effected by measuring and mathematically processing two time periods, the time required for a liquid segment to move past one such apparatus and, also, the time required for the leading edge of the same liquid segment to traverse the distance between the two apparatuses. A variety of techniques are disclosed for minimizing error in such a determination caused by variations in liquid segment flow velocity during the measurement interval.

DETAILED DESCRIPTION OF THE INVENTION

Figure 2B:
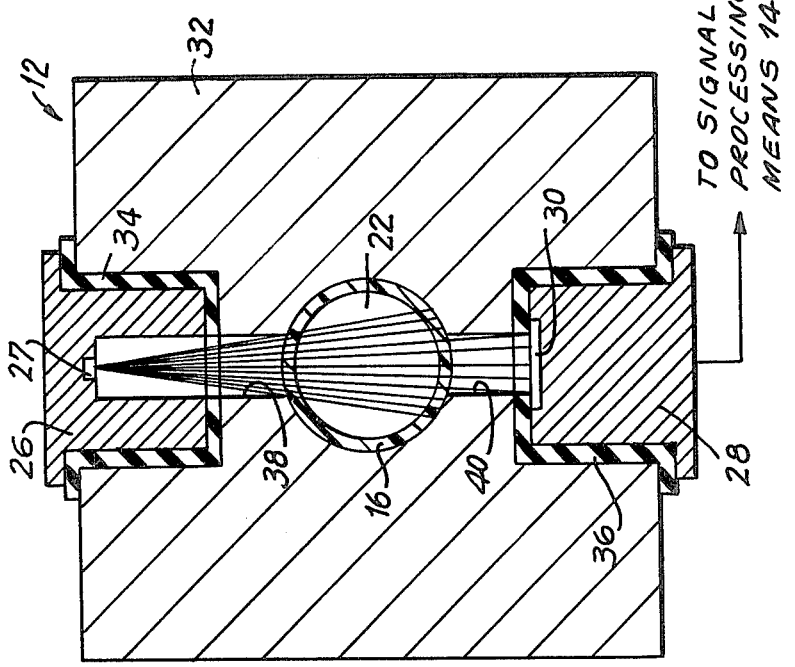
FIGS. 2A and 2B are respectively cross-sectional views, taken generally transversely of a flow conduit, of the apparatus of FIG. 1.
Figure 1:
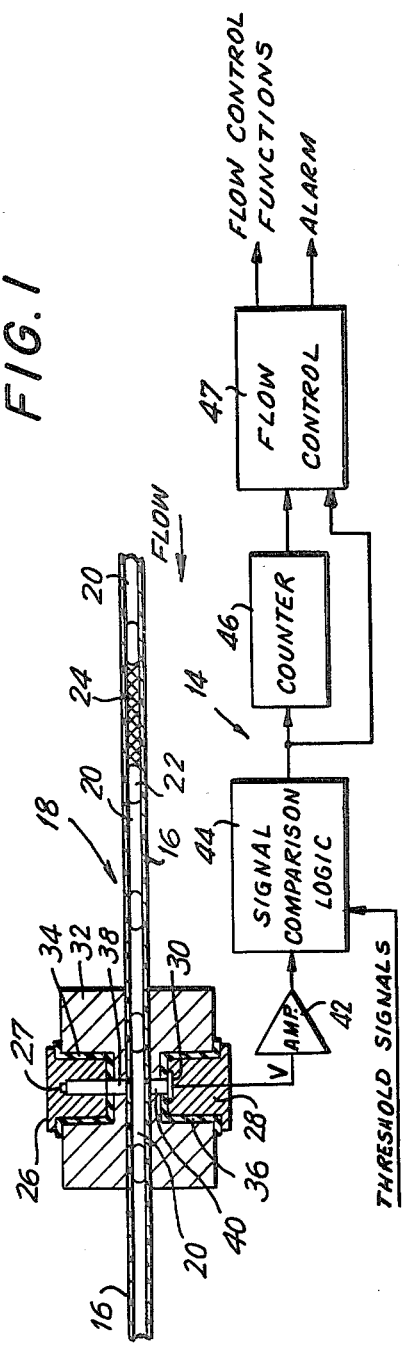
FIG. 1 is a cross-sectional view, taken generally longitudinally of a flow conduit, of a detector apparatus according to the present invention, which includes appropriate signal processing circuitry.
Figure 2A:
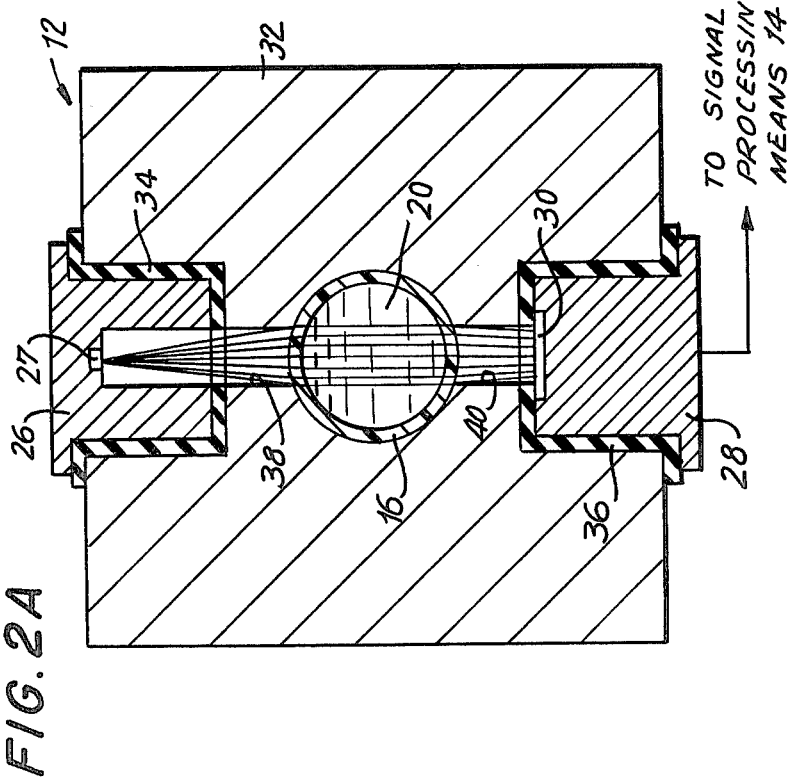

Referring now to FIGS. 1, 2A and 2B, a system embodying the present invention is indicated generally at 10 and comprises gas-liquid interface and segment detection and signal generating means, as indicated generally at 12, and signal processing means as indicated generally at 14.

The signal generating means 12 are operatively associated with an optically transparent conduit 16 through which is flowing a segment liquid stream, generally indicated at 18, comprising alternating segments of liquid 20 and fully occluding separating gas segments. Such gas segments may be formed of an inert gas or air 22. The conduit 16 may, for example, be made of Teflon and form the flow conduit of a single-channel, continuous-flow biochemical analyzer, of the type disclosed in U.S. Pat. No. 3,241,432, assigned to a common assignee. The segmented liquid stream 18 is pumped at a substantially constant flow rate through the conduit 16 with the segments of liquid 20 being constituted, for example, by water, blood sera, etc., appropriately reacted for colorimetric analysis. In addition, at least one of the liquid segments would be constituted by an appropriate marker solution, for example, copper chloride, as indicated at 24 and which is introduced into stream 18 for purposes described hereinbelow.

The signal generating means 12 comprise a source 26, having an active element 27, of infra-red (IR) radiation, for example, a light-emitting diode (LED), and an IR detector 28, for example, a silicon cell having an active element 30, which are operatively disposed at opposite sides of conduit 16 in a metallic housing 32. The IR detector 28 outputs a voltage signal V which is directly proportional to the IR energy from IR source 26 incident upon the active surface 30 of the detector.

The IR source 26 and the IR detector 28 are electrically insulated from housing 32 by insulative bushings or the like, indicated at 34 and 36, respectively.

A generally circular input aperture 38 is defined in housing 32 and bushing 34 to pass the IR energy from source 26 through IR-transparent conduit 16; and a generally circular output aperture 40 is defined in like manner in housing 32 and bushing 36 in alignment with input aperture 38 to pass IR energy directed through conduit 16, and the relevant portion of the stream 18, onto the active surface 30 of detector 28. Disposition of the active surface 30 of detector 28 within housing 32 effectively shields said surface from ambient, extraneous IR energy radiation.

The signal processing means 14 comprises an amplifier 42 connected to the output of detector 28. Signal comparison logic means, indicated schematically at 44, are connected to the output of amplifier 42. The amplified signals V outputted from detector 28 and appropriate threshold signals applied to logic means 44 are described in greater detail hereinbelow. Counter means, indicated at 46, are operative to count the signals outputted from the logic means 44, and flow control means, indicated at 47, are connected to logic means 44 and counter means 46 and are operable to control the configuration of the segmented fluid stream 20 in conduit 16, and to provide an appropriate alarm upon the detection of predetermined variation between actual and desired fluid stream configuration.

For example, to detect each of the air-liquid interfaces in segmented liquid stream 18 and, also to detect each of the marker liquid segments 24, IR energy source 26 is configured to radiate IR energy over a portion of the spectrum centered around a wavelength which is essentially not absorbed or refracted by the water, serum, reagent, or serum-reagent mixture, liquid segments 20. Preferably, at such wavelength, the IR energy transmission characteristics of the respective blood serum and/or reagent segments 20 is substantially the same as those of the water segments 20. By way of example, rather than by way of limitation, this wavelength may range between 800 and 1000 nm.

Figure 3:
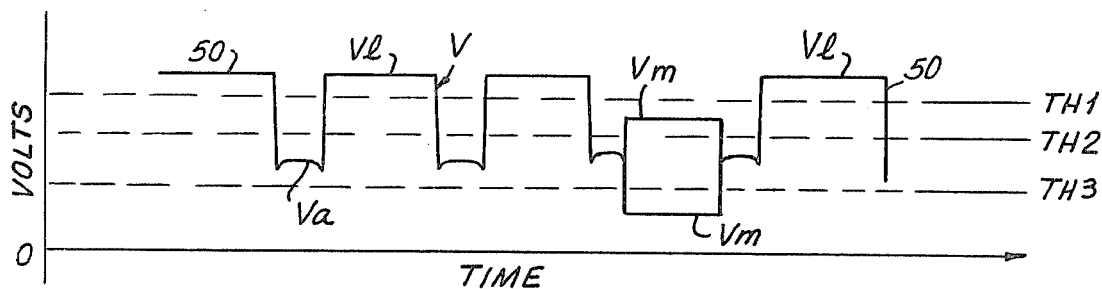
FIG. 3 is a graph depicting the signals outputted by the apparatus of FIG. 1.

Accordingly, passage of one of the liquid segments 20 in conduit 16 between apertures 38 and 40 results in the transmission of a major portion of the IR energy from source 27 to and through conduit 16 and the liquid segment 20 for impingement upon the active surface 30 of detector 28, relatively minimal energy losses due to refraction and/or absorption, all in the manner illustrated in FIG. 2A. This results in the outputting of a signal Vl of relatively high magnitude by detector 28 as illustrated in FIG. 3. For calibration of the signal generating means 12, the magnitude of signal Vl outputted by detector 28 when water, only is flowing through conduit 16 is used as reference level against which would be compared the magnitude of signal Vl when another liquid (or fluid) only, is flowed through conduit 16; any significant variation therebetween is substantially eliminated by appropriate adjustment of the central IR energy radiation wavelength of source 26 and/or of other relevant operational characteristics of the signal generation means 12, to insure general coincidence between the magnitudes of signal Vl irrespective of whether the liquid segment passing through signal generation means is constituted by water, blood serum and/or reagent.

Conversely, when an air segment 22 passes through conduit 16 between apertures 38 and 40, a substantial portion of the IR energy radiated from source 26 will be refracted, or bent away, as a function of the relative IR refractive indexes of air and Teflon, whereby a substantially lesser portion of the IR energy impinges upon the active surface 30 of detector 28 as illustrated in FIG. 2B, with attendant outputting by the latter of a signal Va of relatively low magnitude, again as illustrated in FIG. 3.

Liquid marker segment 24 may be constituted by any practical substance with not substantial IR energy absorbance characteristics at the central wavelength chosen for IR source 26. For example, a solution of copper chloride has proven particularly appropriate for use as the marker liquid. Since the IR energy absorbance of such solution depends largely upon concentration, choice of an appropriate concentration for the marker liquid solution results in the outputting by detector 28 of a signal Vm of magnitude less than signal Vl and greater than signal Va or of a signal Vm of magnitude less than signal Va upon passage of a marker liquid segment 24 between apertures 38 and 40.

Accordingly, flow of the segmented liquid stream 18 in the indicated direction through conduit 16 and signal generation means 12 results in the outputting by detector 28 of a signal V, having generally the waveform indicated at 50 in FIG. 3. More specifically, signals Vl and Va are outputted from detector 28 coincident with passage of liquid segments 20 and air segments 22 through signal generation means 12. In addition, the passage of marker liquid segment 24 through signal generation means 12 results in the outputting by detector 28 of a signal Vm which, as depicted, may be of greater or lesser amplitude than the signal Va, depending upon the concentration of the marker liquid, as discussed hereinabove, but readily distinguishable from the signals Vl and Va.

Threshold signals applied to logic means 44 are indicated in dashed lines as TH1, TH2 and TH3, respectively, and are superimposed for clarity of description upon waveform 50 of FIG. 3. Threshold signal TH1 is predetermined to be of lower level than the Vl signals and of higher level than the Va signals and the higher level Vm signals (assuming a liquid marker segment 24 of relatively low concentration is used). Threshold signal TH2 is predetermined to be of lower level than the higher level Vm signals and of higher level than the Va signals. Threshold signal TH3 is predetermined to be of lower level than all of the other signals.

Under the above conditions, the concomitant application of the respective detector signals V and threshold signals TH1, TH2 and TH3, to logic means 44 provides the capability of accurately and reliably differentiating between the air, blood serum and/or reagent, and marker liquid segments passing through conduit 16 in a completely non-invasive manner. More specifically, in each instance that the level of output signal V exceeds the level of threshold signal TH1, logic means 44 outputs a signal to counter 46, which is indicative of the passage of a blood serum and/or reagent liquid segment 20 through the detector means 12. Alternatively, in each instance that the level of signal V is greater than that of threshold signal TH2 but lesser than that of threshold signal TH1, logic means 44 outputs a signal to counter 46 indicative of the passage of a marker liquid segment 24 through the detector means 12. Also, in each instance that the level of signal V is lesser than that of threshold signal TH2, logic means 44 outputs a signal to counter 46 indicative of the passage of an air segment 22 through detector means 12. In addition, waveform 50 of FIG. 3 indicates that the commencement and termination of the passage of an air segment 22 through the detector means 12 are precisely indicated by the commencement and termination of the outputting of signal Va by detector 28.

Signal comparison logic 44, however, it set not to respond to the fast-transition signals between levels. It only produces an output when the signal V is of greater duration than the shortest expected duration, for example, of signal Va.

Accordingly, system 10 provides a precise detection of each air-liquid segment interface and, also, a precise count of and accurate differentiation between the respective liquid and air segments of said segmented stream passing through conduit 12. In addition, the incorporation of one or more marker liquid segments in such segmented stream provides reference points from which counting can be commenced, or at which counting can be terminated. Thus will readily be understood by those skilled in this art that application as indicated of the respective output signals from logic means 44 and counter means 46 to flow control means 47 will enable system 10 to precisely monitor, synchronize and control the configuration of segmented fluid stream 18 with regard to segment number and sequence of said segmented fluid stream.

The non-invasive, precise determination of the respective volumes of the liquid segments 20 of the segmented liquid stream 18 is achieved by the arrangement illustrated in FIGS. 4 through 8. As indicated generally at 52 in FIG. 4, the arrangement comprises two spaced signal generation means, indicated at 12A and 12B, relative to the conduit 16, such that the respective apertures 38A, 40A and 38B, 40B are precisely spaced a predetermined distance D. Liquid segment volume determination is based upon the precise measurement of the time duration TA required for passage of an entire liquid segment 20A in conduit 16 between the aligned apertures 38A and 40A of signal generating means 12A and upon the precise measurement of the time TD required for passage of the leading edge of the liquid segment 20A between apertures 38A and 40A of signal generating means 12A and apertures 38B and 40B of signal generating means 12B. Since time TA is directly proportional to the volume of the liquid segment 20A and indirectly proportional to the flow velocity along conduit 16 and time TD is indirectly proportional to flow velocity only, the segment flow velocity factor is effectively eliminated from the required calculations by simply taking the ratio of time TA to time TD, as described hereinbelow.

The signal processing means, indicated generally at 54, for liquid segment volume determination comprises amplifier 56 and signal comparison logic means 58 to which signal V outputted from detector 28A is applied and, also, amplifier 60 and signal comparison logic means 62 to which signal V outputted from detector 28B is applied. Threshold signals TH1 are applied to signal comparison logic means 58 and 62. As only detector output signals resulting from passage of liquid segments 20 through the respective signal generation means 12A and 12B are relevant to the volume determination of liquid segments other than the marker segment, the requirement for threshold signals TH2 and TH3 is eliminated. TH2 and TH3 signals are not required if the volume of the marker segment 28 is not desired. However, in the general case where the volume of all of the different fluid segments are desired, all three thresholds are required. The signals outputted from signal comparison logic means 58 and 62 are concomitantly applied to data processing logic means 64, the output of the latter being applied to segment volume computation logic means 66, for segment volume computation, as described hereinbelow. Flow control means are indicated at 67 in FIG. 4 and are operable, in accordance with the signals applied thereto as shown from segment volume computation logic means 66, to control the respective segment volumes of the segmented fluid stream 18 and to provide an appropriate alarm upon the detection of predetermined variation between actual and desired segment volumes.

Figure 5A:
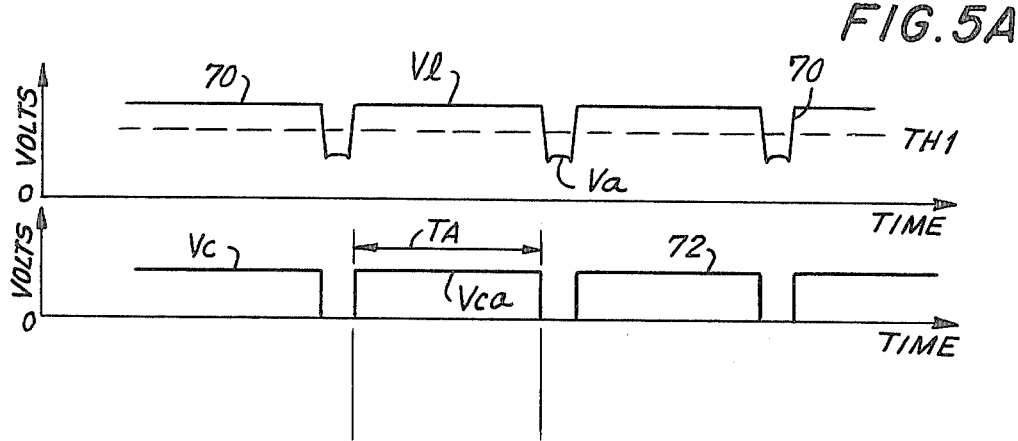
FIGS. 5A and 5B are graphs depicting the signals outputted by the detector apparatus of FIG. 4.
Figure 5B:
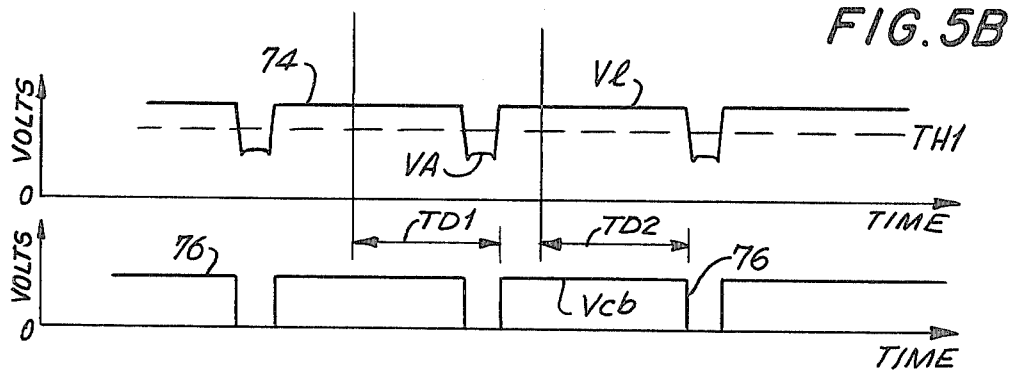

The respective signal outputs of the signal generation means 12A and 12B and of signal comparison logic means 58 and 62 are depicted on a same time scale in FIGS. 5A and 5B. More specifically, waveform 70 of FIG. 5A illustrates signals Vl outputted by detector 28A attendant the passage of liquid segments 20 between apertures 38A and 40A and the signals Va outputted thereby attendant the passage of the air segments 22 between such apertures. Threshold signal TH1 is superimposed in dashed fashion on waveform 70 for clarity of description. Concomitant application of waveform 70 and threshold signal TH1 to signal comparison logic means 58 results in the outputting by the latter of the signals Va having the waveform depicted at 72 in FIG. 5A. Comparison of waveforms 70 and 72 of FIG. 5A reveals that the transit time TA of a liquid segment 20 through signal generation means 12A is precisely determined by the time duration of specifically identified signal pulse Vca as outputted from signal comparison logic means 58. The commencement and termination of signal Vca will coincide in time precisely with the passage of the leading and trailing edges, respectively, of that liquid segment between apertures 38A and 40A of signal generation means 12. Waveform 74 of FIG. 5B illustrates signals V1 outputted by detector 28B attendant the passage of the liquid segments 20 between apertures 38B and 40B, and illustrates the signals Va outputted thereby attendant the passage of air segments 22 between those apertures. Threshold signal TH1 is superimposed in dashed fashion on waveform 74. Concomitant application of waveform 74 and threshold signal waveform TH1 to signal-comparison logic means 62 of FIG. 4 results in the outputting by the latter of the signals Vc having the waveform depicted at 76 in FIG. 5B. Again, waveforms 74 and 76 illustrate that the transit time TA of a liquid segment 20A through signal generation means 12B is precisely determined by the time duration of specifically identified signal pulse Vcb as outputted from signal comparison logic means 62. In addition, comparison of the respective waveforms 72 and 76 shown in FIGS. 5A and 5B, respectively, makes clear that the time TD1 required for the leading edge of liquid segment 20 to traverse the distance D of FIG. 4 between signal generating means 12A and 12B, and the time TD2 for the trailing edge of such liquid segment to traverse a same distance D are each precisely determined.

Figure 6:
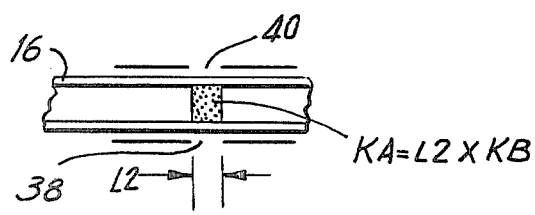
FIGS. 6 and 7 are respectively cross-sectional views taken generally longitudinally of the flow conduit to identify various dimensions of interest.
Figure 7:
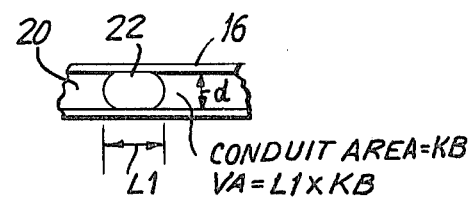

Precise determination of the respective volumes of the liquid segments 20 is effected by data processing logic means 64 and segment volume computation logic means 66 in accordance with the following equations and reference is here made to FIGS. 6 and 7 for illustration of relevant terms of those equations.

More specifically, and taking first the situation wherein the velocity of the liquid segment 20 is constant during the measurement interval between signal generation means 12A and 12B it may be understood that:

$$TA = (L1 - L2)/SV \text{ and} \tag{1}$$

$$L1 = VL/KB \text{ and } L2 = KA/KB \tag{2}$$

wherein:
VL = liquid segment volume,
L1 = liquid segment length,
L2 = optical aperture length,
KB = cross sectional area of conduit 16,
VA = air segment volume,
KA = effective optical aperture volume, and
SV = velocity of the liquid segment in conduit 16.
Substituting terms in Equation 1 leads to:

$$TA = ((VL/KB) - )KA/KB)/SV = (VL - KA)/(KB \times SV), \text{ while} \tag{3}$$

$$TD1 = D/SV. \tag{4}$$

Division of Equation 3 by Equation 4 leads to:

$$TA/TD1 = (VL - KA)/(KB \times D) = (VL - KA)/KC \tag{5}$$

wherein:
KC = volume of conduit 16 between the respective signal generation means 12A and 12B.

Solution of Equation 5 for liquid segment volume VL leads to the following:

$$VL = KC \times (TA/TD1) + KA. \tag{6}$$

Since each of KA and KC are constants which are precisely determined by appropriate calibration or physical measurement, the volume VL of the liquid segment in question is readily determined by segment volume computation logic 66, by determination by data processing logic means 64 of the respective values for times TA and TD1 of FIGS. 5A and 5B.

Accordingly, two independent measurements TA and TD1 are required. The TD1 measurement is necessary to negate the effects of velocity in the computation. As seen from equation 3, the TA measurement represents the time for a liquid segment to pass the first pair of apertures and is proportional to the volume of such segment VL and inversely proportional to the velocity. To determine the liquid segment VL independently of the velocity, an independent velocity measurement is made by measuring the time TD1 for the segment to move a fixed distance D, resulting in the SV measurement of Equation 4. By taking the ratio of equations 3 to 4, the velocity term is eliminated from the final computation of the liquid sample volume, as shown in equation 6.

In certain instances, the liquid segment velocity SV in conduit 16 may change during the segment velocity measurement interval, for example, due to the introduction of additional fluids into segmented stream 18 upstream and/or downstream in conduit 16 of the respective signal generation means 12A and 12B during passage of such liquid segment between such signal generation means. In such event, the liquid segment velocity SV during the time interval TA may differ from that during the time interval TD1. Accordingly, determination of the liquid segment volume VL by computation logic means 66 in strict accordance with Equation 6 can result in error, the magnitude of such error being dependent on the timing and extent of the change(s) in liquid segment velocity. Minimization of this error is possible by utilization of the time interval TD2 of FIG. 5B, and by utilization of appropriate weighting factors, to provide a more accurate, average time interval term for use in Equation 6.

More specifically, this more accurate, average time interval term TDA is determined as follows:

$$TDA = R1 \times TD1 + R2 \times TD2 \tag{7}$$

wherein:
R1 and R2 are weighting factors which are dependent upon the respective ratio of TD1 and TD2 to Ta.

Substitution of the average time interval term TDA for the time interval term TD1 in Equation 6 leads to the following:

$$VL = KC \times (TA/TDA) + KA. \tag{8}$$

Figure 8:
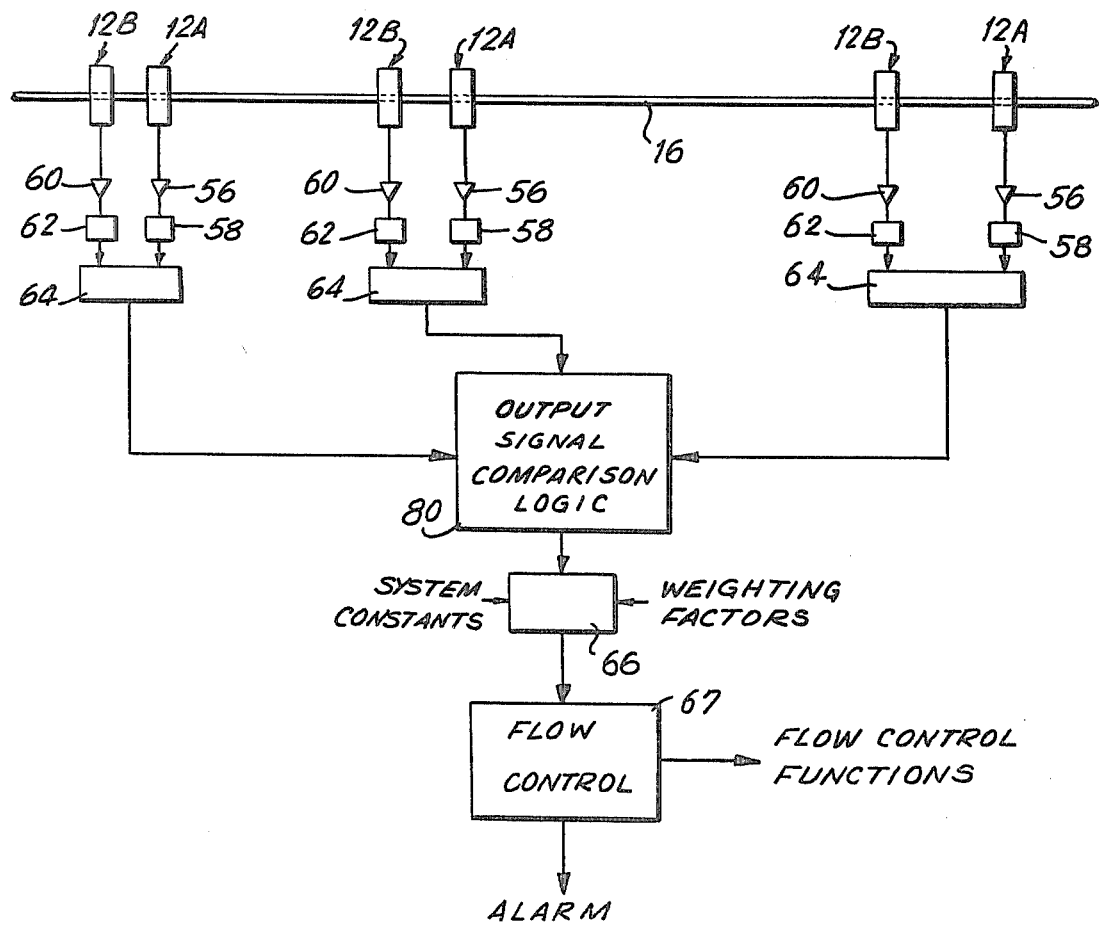
FIG. 8 is a schematic diagram of a plurality of detector apparatuses operatively disposed along a same flow conduit.

Accuracy of liquid segment volume determination when liquid segment velocity SV is not constant during the segment measurement can alternatively be achieved by use of multiple pairs of the signal generation means 12 spaced at different distances along conduit 16, so that one of said distances or spacings D is most appropriate for each flow condition existing in conduit 16, all as depicted in schematic form in FIG. 8. Despite velocity changes during the measurement interval, if time interval TA is made essentially equal to time interval TD1, no error results, since both TA and TD1 measurements are equally subject to any transient velocity effects, since both are made over the same time interval. Under these circumstances, output signal comparison logic means indicated at 80 is provided to compare the TA and TD1 signals outputted from the respective data processing logic means 64 of each pair of the signal generation means 12A and 12B and determine which of said pairs is outputting TA and TD1 signals which are most nearly equal, thereby indicating the most nearly constant liquid segment velocity SV between that pair. The TA signals will, of course, be directly proportional to liquid segment volume VL and inversely proportional to liquid segment velocity SV, while the TD1 signals will be proportional only to liquid segment velocity SV. In such instance, those most nearly equal TA and TD1 signals would be outputted, as indicated, from output signal comparison logic means 80 to segment volume computation logic means 66 for segment volume determination.

Figure 4:
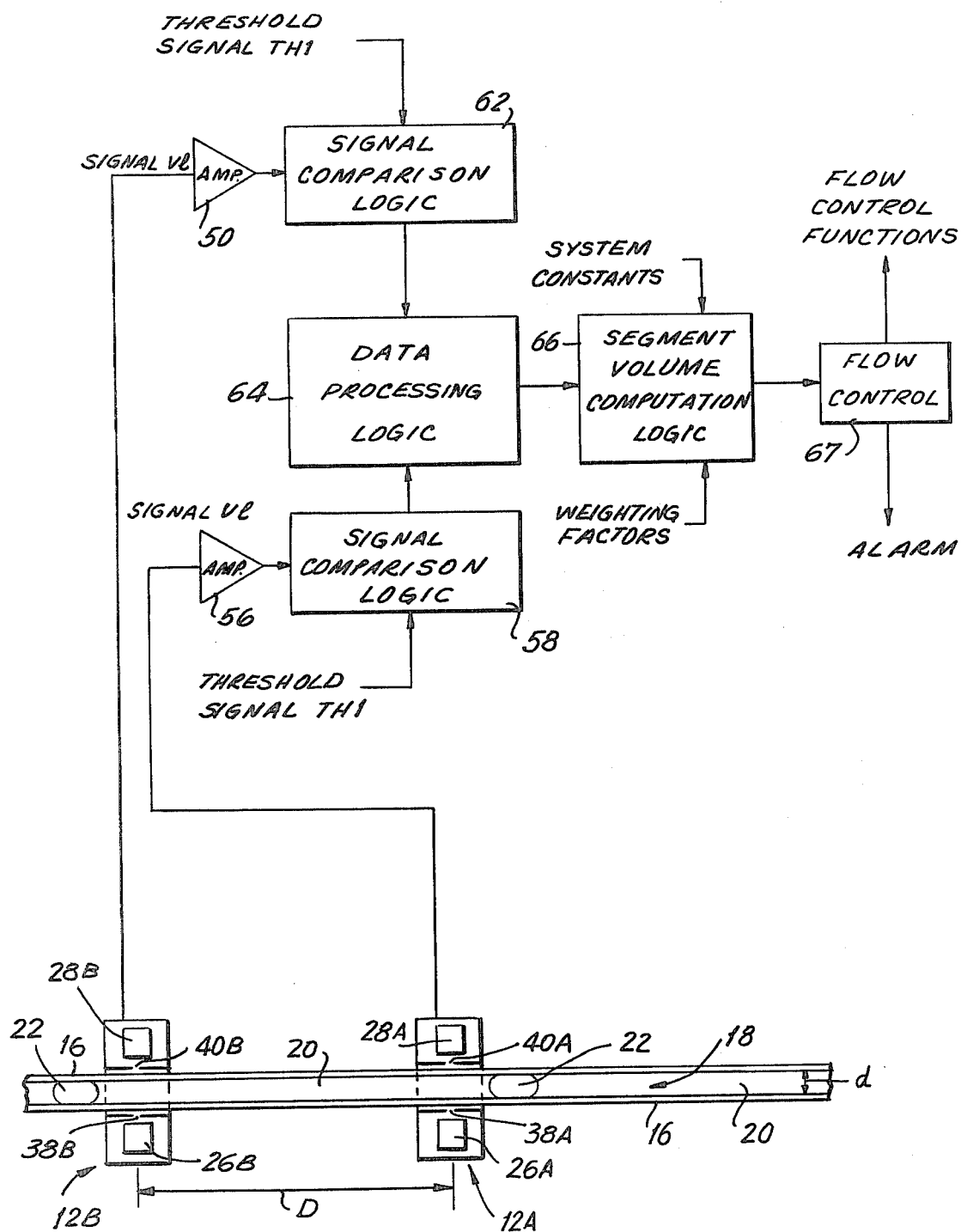
FIG. 4 is a generally schematic depiction of the detector apparatus of FIG. 1 operatively disposed relative to a flow conduit.

As a further alternative for accurate liquid segment volume determination in instances wherein liquid segment velocity SV is not constant along conduit 16, a single pair of signal generation means 12 can be utilized, as illustrated in FIG. 4, but disposed relative to conduit 16 at a location as far downstream on the latter as practicable so that the effects of transient velocity changes in the segmented liquid stream 18 will be minimized at such location.

By the above is believed made clear that liquid segment volume determination to a high degree of accuracy, despite changes in liquid segment velocity SV during the measurement interval, is nonetheless provided by the system of my invention through the determination by data processing logic means 64 of the respective values for RA, TD1 and TD2 of FIGS. 5A and 5B, only, and again in full accordance with the stated objects of that system.

A representative utilization of the method and apparatus of my invention with regard to segmented fluid stream 18 for the non-invasive detection of the gas-liquid interfaces and the liquid and gas segments, and the concomitant determination of the liquid segment volumes of said fluid stream, is depicted schematically in FIG. 9 and will be seen therein to comprise the operable disposition of spaced signal generation means 12A and 12B relative to conduit 16, the application of the signals outputted from signal generation means 12A to signal processing means 14 for interface and segment detection as described in detail hereinaove, and the application of the signals outputted from signal generation means 12A and 12B to segment volume determination signal processing means as there indicated generally at 82 for segment volume determination, again as described in detail hereinabove. In this instance, concomitant application as depicted of the interface, segment and segment volume signals from signal processing means 14 and 82 to flow control means 67 will, of course, provide for the precise monitoring, synchronization and control of the segmented fluid stream 20 with regard to segment member, sequence and volume to significant advantage.

Various changes may of course be made in my invention as depicted and described hereinabove without departing from the spirit and scope thereof as defined in the appended claims.

What is claimed is:

1. In apparatus for the detection of the respective segments, and the respective segment interfaces, of a continuous fluid stream which comprises alternating fluid segments flowing in an optionally transparent conduit, said fluid segments having different radiation energy absorbance and/or refraction characteristics, the improvements comprising, radiation energy source means disposed without said conduit and operable to irradiate the same and said flowing fluid stream, radiation energy detecting means disposed without said conduit and operable to detect the radiation energy from said source means which is transmitted through said conduit and said flowing fluid stream, and to output a signal indicative thereof, and means to process said output signal to indicate said fluid segments and said segment interfaces, respectively, wherein, said fluid segments comprise segments of liquids, and wherein the spectral content of said radiation energy is generally outside the radiation energy absorbance range of said liquids.

2. In apparatus as in claim 1 wherein, said fluid segments comprise a segment of a marker liquid, and wherein the spectral content of said radiation energy is generally within the radiation energy absorbance range of said marker liquid.

3. In apparatus as in claim 1 wherein, said fluid segments comprise segments of air.

4. In apparatus as in claim 1 wherein, said radiation energy is infra red energy.

5. In apparatus as in claim 4 wherein, the spectral content of said infra red energy is centered around a wavelength ranging between 800 and 1000 nm.

6. In apparatus as in claim 5 wherein, said fluid segments comprise blood serum and/or reagent segments, water segments, and air segments.

7. In apparatus for the determination of the respective liquid segment volumes of a continuous fluid stream which comprises alternating liquid and other fluid segments flowing in an optically transparent conduit, said liquid segments having different radiation energy absorbance and/or refraction characteristics than said other fluid segments, the improvements comprising, radiation energy source means disposed without said conduit and operable to irradiate the same and said flowing fluid stream at spaced locations along said conduit, radiation energy detecting means disposed without said conduit and operable to detect the radiation energy from said source means which is transmitted through said conduit and said flowing fluid stream at said spaced locations, and to output signals indicative thereof, and means to process said output signals to determine said liquid segment volumes.

8. In apparatus as in claim 7 wherein, said radiation energy source means comprise first and second radiation energy sources disposed at said spaced locations along said conduit to one side thereof, and said radiation energy detecting means comprise first and second radiation energy detectors disposed to the opposite side of said conduit at said spaced locations in optical alignment with said first and second radiation energy sources, respectively.

9. In apparatus as in claim 7 wherein, the spectral content of said radiation energy is generally outside the radiation energy absorbance range of said liquids.

10. In apparatus as in claim 9 wherein, the spectral content of said infra red energy is centered around a wavelength ranging between 800 and 1000 nm.

11. In apparatus as in claim 7 wherein, said fluid segments comprise segments of air.

12. In apparatus as in claim 7 wherein, said radiation energy is infra red energy.

13. In apparatus as in claim 7 wherein, said signal processing means comprise means to determine the time required for one of said liquid segments to flow in said conduit past one of said locations, and the time required for the leading edge of the same one of said liquid segments to flow in said conduit between locations.

14. In apparatus as in claim 13 wherein, said signal processing means further comprise means to determine the time required for the trailing edge of said one of said liquid segments to flow in said conduit between said locations.

15. In a method for the detection of the respective segments, and the respective segment interfaces, of a continuous fluid stream which comprises alternating fluid segments flowing in an optically transparent conduit, said fluid segments having different radiation energy absorbance and/or refraction characteristics and comprising liquid segments, the improvements comprising the steps of, irradiating said conduit and said flowing fluid stream with radiation energy having a spectral content which is generally outside the radiation energy absorbance range of said liquid segments, detecting the irradiating radiation energy which is transmitted through said conduit and said flowing fluid stream and providing a signal indicative thereof, and processing said signal to indicate said fluid segments and said segment interfaces, respectively.

16. In a method as in claim 15 wherein, said fluid segments comprise segment of a marker liquid, and wherein the spectral content of said radiation energy is generally within the radiation energy absorbance range of said marker liquid.

17. In a method as in claim 15 wherein, the step of irradiating said conduit and said flowing fluid stream comprises the irradiation thereof with infra red energy.

18. In a method as in claim 17 wherein, the step of irradiating said conduit and said flowing fluid stream comprises the irradiation thereof with infra red energy having a spectral content centered around a wavelength ranging between 800 and 1000 nm.

19. In a method for the determination of the respective liquid segment volumes of a continuous fluid stream which comprises alternating liquid and other fluid segments flowing in an optically transparent conduit, said liquid segments having different radiation energy absorbance and/or refraction characteristics than said other fluid segments, the improvements comprising the steps of, irradiating said conduit and said flowing fluid stream with radiation energy at spaced locations along said conduit, said radiation energy having a spectral content which is generally outside the radiation energy absorbance range of said liquid segments, detecting the irradiating radiation energy which is transmitted through said conduit and said flowing fluid stream at said spaced locations and providing signals indicative thereof, and processing said signals to determine said liquid segment volumes.

20. In a method as in claim 19 wherein, the step of irradiating said conduit and said flowing fluid stream comprises the irradiation thereof with infra red energy.

21. In a method as in claim 20 wherein, the step of irradiating said conduit and said flowing fluid stream comprises the irradiation thereof with infra red energy having a spectral content centered around a wavelength ranging between 800 and 1000 nm.

22. In a method as in claim 19 wherein, the processing of said signals comprises the determination of the time required for one of said liquid segments to flow in said conduit past one of said locations, and the time required for the leading edge of the same one of said liquid segments to flow in said conduit between locations.

23. In a method as in claim 22 wherein, the processing of said signals further comprises the determination of the time required for the trailing edge of the same one of said liquid segments to flow in said conduit between said locations.

24. In apparatus for the detection of the segments and segment interfaces, and for the determination of the liquid segment volumes, respectively, of a continuous fluid stream which comprises alternating liquid and other fluid segments flowing in an optically transparent conduit, said liquid segments having different radiation energy absorbance and/or refraction characteristics than said other fluid segments, the improvements comprising, radiation energy source means disposed without said conduit and operable to irradiate the same and said flowing fluid stream at spaced locations along said conduit, radiation energy detecting means disposed without said conduit and operable to detect the radiation energy from said source means which is transmitted through said conduit and said flowing fluid stream at said spaced locations and to output signals indicative thereof, means to process said output signals to indicate said segments and said segment interfaces, respectively, and means to process said output signals to determine said liquid segment volumes.

25. In a method for the detection of the segments and segment interfaces, and for the determination of the liquid segment volumes, respectively, of a continuous fluid stream which comprises alternating liquid and other fluid segments flowing in an optically transparent conduit, said liquid segments having different radiation energy absorbance and/or refraction characteristics than said other fluid segments, the improvements comprising the steps of, irradiating said conduit and said flowing fluid stream with radiation energy at spaced locations along said conduit, detecting the irradiating radiation energy which is transmitted through said conduit and said flowing fluid stream at said spaced locations and providing signals indicative thereof, and processing said signals to indicate said segments and segment interfaces and to determine said liquid segment volumes.

26. In a method for determining thee volume of a discrete fluid segment flowing in a conduit in a continuous flowing stream, said fluid segment being disposed in said stream between two other fluid segments each defining an interface with said fluid segment, the improvements comprising the steps of measuring a first time period required for one of said interfaces to flow between two spaced locations along said conduit, measuring a second time period required for said fluid segment to flow between said spaced locations, and relating said first and second time periods to determine the volume of said fluid segment.

* * * * *